(12) United States Patent
Chu et al.

(10) Patent No.: US 8,398,660 B2
(45) Date of Patent: Mar. 19, 2013

(54) SUTURING INSTRUMENT

(75) Inventors: Michael S. H. Chu, Brookline, MA (US); Greg R. Furnish, Louisville, KY (US); William C. Mers Kelly, Crestwood, KY (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 13/350,270

(22) Filed: Jan. 13, 2012

(65) Prior Publication Data

US 2012/0109163 A1    May 3, 2012

Related U.S. Application Data

(63) Continuation of application No. 10/921,517, filed on Aug. 19, 2004, now Pat. No. 8,123,762.

(51) Int. Cl.
*A61B 17/04* (2006.01)
*A61B 17/12* (2006.01)

(52) U.S. Cl. ........................................ 606/144
(58) Field of Classification Search ............. 606/144
See application file for complete search history.

(56) References Cited

U.S. PATENT DOCUMENTS

| | | | |
|---|---|---|---|
| 342,773 A | 6/1886 | Bailey | |
| 919,138 A | 4/1909 | Drake et al. | |
| 1,037,864 A | 9/1912 | Carlson et al. | |
| 1,449,087 A | 3/1923 | Bugbee | |
| 1,815,725 A | 7/1931 | Pilling et al. | |
| 1,822,330 A | 9/1931 | Ainslie | |
| 2,577,240 A | 12/1951 | Findley | |
| 2,579,192 A | 12/1951 | Kohl | |
| 3,013,559 A | 12/1961 | Thomas | |
| 3,160,157 A | 12/1964 | Chisman | |
| 3,470,875 A | 10/1969 | Johnson | |
| 3,638,653 A | 2/1972 | Berry | |
| 3,840,017 A | 10/1974 | Violante | |
| 3,871,379 A | 3/1975 | Clarke | |
| 3,918,455 A | 11/1975 | Coplan | |
| 3,946,740 A | 3/1976 | Bassett | |
| 3,986,468 A | 10/1976 | Szostak et al. | |
| 4,161,951 A | 7/1979 | Scanlan, Jr. | |
| 4,164,225 A | 8/1979 | Johnson et al. | |
| 4,224,947 A | 9/1980 | Fukuda | |
| 4,235,177 A | 11/1980 | Arbuckle | |
| 4,235,238 A | 11/1980 | Ogiu et al. | |

(Continued)

FOREIGN PATENT DOCUMENTS

DE    41 24 383 C1    5/1992
EP    0 140 557    5/1985

(Continued)

OTHER PUBLICATIONS

Description of "Rema Deep Suture," publication status and dates unknown, original document in German, English translation attached.

(Continued)

*Primary Examiner* — Melanie Tyson
(74) *Attorney, Agent, or Firm* — Brown Rudnick LLP

(57) ABSTRACT

The suturing instrument includes an elongate member having an articulating distal portion biased offset from the elongate member, and a sheath slideably disposed about the elongate member. The user positions the sheath in contact with the articulating distal portion to actuate the distal portion relative to the elongate member. The articulating distal portion is pivotally coupled to the elongate member for improved maneuverability within the body of a patient during surgical procedures.

9 Claims, 14 Drawing Sheets

U.S. PATENT DOCUMENTS

| | | |
|---|---|---|
| 4,236,470 A | 12/1980 | Stenson |
| 4,244,372 A | 1/1981 | Kapitanov et al. |
| 4,312,337 A | 1/1982 | Donhue |
| 4,345,601 A | 8/1982 | Fukuda |
| 4,442,964 A | 4/1984 | Becht |
| 4,452,157 A | 6/1984 | Cantada et al. |
| 4,471,781 A | 9/1984 | Di Giovanni et al. |
| 4,491,135 A | 1/1985 | Klein |
| 4,493,323 A | 1/1985 | Albright et al. |
| 4,548,202 A | 10/1985 | Duncan |
| 4,557,265 A | 12/1985 | Andersson |
| 4,579,072 A | 4/1986 | Koike et al. |
| 4,596,249 A | 6/1986 | Freda et al. |
| 4,602,635 A | 7/1986 | Mulhollan et al. |
| 4,621,640 A | 11/1986 | Mulhollan et al. |
| 4,635,638 A | 1/1987 | Weintraub et al. |
| 4,762,128 A | 8/1988 | Rosenbluth |
| 4,762,260 A | 8/1988 | Richards et al. |
| 4,781,190 A | 11/1988 | Lee |
| 4,890,615 A | 1/1990 | Caspari et al. |
| 4,893,623 A | 1/1990 | Rosenbluth |
| 4,898,155 A | 2/1990 | Ovil et al. |
| 4,899,746 A | 2/1990 | Brunk |
| 4,923,461 A | 5/1990 | Caspari et al. |
| 4,926,860 A | 5/1990 | Stice et al. |
| 4,935,027 A | 6/1990 | Yoon |
| 4,955,859 A | 9/1990 | Zilber |
| 4,957,498 A | 9/1990 | Caspari et al. |
| 4,994,066 A | 2/1991 | Voss |
| 5,015,250 A | 5/1991 | Foster |
| 5,037,433 A | 8/1991 | Wilk et al. |
| 5,047,039 A | 9/1991 | Avant et al. |
| 5,059,169 A | 10/1991 | Zilber |
| 5,067,957 A | 11/1991 | Jervis |
| 5,100,415 A | 3/1992 | Hayhurst |
| 5,100,418 A | 3/1992 | Yoon et al. |
| 5,100,421 A | 3/1992 | Christoudias |
| 5,100,498 A | 3/1992 | Takeuchi et al. |
| 5,152,769 A | 10/1992 | Baber |
| 5,171,257 A | 12/1992 | Ferzli |
| 5,181,919 A | 1/1993 | Bergman et al. |
| 5,188,636 A | 2/1993 | Fedotov |
| 5,224,948 A | 7/1993 | Abe et al. |
| 5,246,445 A | 9/1993 | Yachia et al. |
| 5,257,999 A | 11/1993 | Slanetz, Jr. |
| 5,258,011 A | 11/1993 | Drews |
| 5,261,917 A | 11/1993 | Hasson et al. |
| 5,275,614 A | 1/1994 | Haber et al. |
| 5,281,237 A | 1/1994 | Gimpelson |
| 5,282,809 A | 2/1994 | Kammerer et al. |
| 5,306,281 A | 4/1994 | Beurrier |
| 5,308,353 A | 5/1994 | Beurrier |
| 5,312,436 A | 5/1994 | Coffey et al. |
| 5,318,577 A | 6/1994 | Li |
| 5,322,501 A | 6/1994 | Mahmud-Durrani |
| 5,324,298 A | 6/1994 | Phillips et al. |
| 5,330,488 A | 7/1994 | Goldrath |
| 5,336,231 A | 8/1994 | Adair |
| 5,354,309 A | 10/1994 | Schnepp-Pesch et al. |
| 5,364,408 A | 11/1994 | Gordon |
| 5,374,275 A | 12/1994 | Bradley et al. |
| 5,383,928 A | 1/1995 | Scott et al. |
| 5,387,221 A | 2/1995 | Bisgaard |
| 5,389,103 A | 2/1995 | Melzer et al. |
| 5,391,174 A | 2/1995 | Weston |
| 5,417,699 A | 5/1995 | Klein et al. |
| 5,417,700 A | 5/1995 | Egan |
| 5,423,833 A | 6/1995 | Zauza |
| 5,425,737 A | 6/1995 | Burbank et al. |
| 5,441,507 A | 8/1995 | Wilk |
| 5,454,823 A | 10/1995 | Richardson et al. |
| 5,458,609 A | 10/1995 | Gordon et al. |
| 5,470,338 A | 11/1995 | Whitfield et al. |
| 5,474,565 A | 12/1995 | Trott |
| 5,474,568 A | 12/1995 | Scott |
| 5,477,794 A | 12/1995 | Klundt |
| 5,496,334 A | 3/1996 | Klundt et al. |
| 5,499,990 A | 3/1996 | Schulken et al. |
| 5,514,178 A | 5/1996 | Torchio |
| 5,518,498 A | 5/1996 | Lindenberg et al. |
| 5,520,703 A | 5/1996 | Essig et al. |
| 5,522,820 A | 6/1996 | Caspari et al. |
| 5,527,321 A | 6/1996 | Hinchliffe |
| 5,527,322 A | 6/1996 | Klein et al. |
| 5,536,273 A | 7/1996 | Lehrer |
| 5,540,704 A | 7/1996 | Gordon et al. |
| 5,540,705 A | 7/1996 | Meade et al. |
| 5,540,713 A | 7/1996 | Schnepp-Pesch et al. |
| 5,549,617 A | 8/1996 | Green et al. |
| 5,562,686 A | 10/1996 | Sauer et al. |
| 5,569,270 A | 10/1996 | Weng |
| 5,571,119 A | 11/1996 | Atala |
| 5,573,540 A | 11/1996 | Yoon |
| 5,573,542 A | 11/1996 | Stevens |
| 5,575,800 A | 11/1996 | Gordon |
| 5,578,044 A | 11/1996 | Gordon et al. |
| 5,582,617 A | 12/1996 | Klieman et al. |
| 5,591,177 A | 1/1997 | Lehrer |
| 5,591,179 A | 1/1997 | Edelstein |
| 5,593,421 A | 1/1997 | Bauer |
| 5,601,578 A | 2/1997 | Murphy |
| 5,613,974 A | 3/1997 | Andreas et al. |
| 5,613,975 A | 3/1997 | Christy |
| 5,618,290 A | 4/1997 | Toy et al. |
| 5,632,751 A | 5/1997 | Piraka |
| 5,632,752 A | 5/1997 | Buelna |
| 5,643,294 A | 7/1997 | Tovey et al. |
| 5,653,717 A | 8/1997 | Ko et al. |
| 5,662,663 A | 9/1997 | Shallman |
| 5,662,664 A | 9/1997 | Gordon et al. |
| 5,662,666 A | 9/1997 | Onuki et al. |
| 5,665,096 A | 9/1997 | Yoon |
| 5,690,269 A | 11/1997 | Bolanos et al. |
| 5,690,652 A | 11/1997 | Wurster et al. |
| 5,690,653 A | 11/1997 | Richardson et al. |
| 5,700,272 A | 12/1997 | Gordon et al. |
| 5,700,273 A | 12/1997 | Buelna et al. |
| 5,702,408 A | 12/1997 | Wales et al. |
| 5,707,378 A | 1/1998 | Ahn et al. |
| 5,707,386 A | 1/1998 | Schnepp-Pesch et al. |
| 5,709,693 A | 1/1998 | Taylor |
| 5,713,908 A | 2/1998 | Jameel et al. |
| 5,713,910 A | 2/1998 | Gordon et al. |
| 5,728,113 A | 3/1998 | Sherts |
| 5,741,276 A | 4/1998 | Poloyko et al. |
| 5,741,277 A | 4/1998 | Gordon et al. |
| 5,741,278 A | 4/1998 | Stevens |
| 5,741,279 A | 4/1998 | Gordon et al. |
| 5,755,727 A | 5/1998 | Kontos |
| 5,759,188 A | 6/1998 | Yoon |
| 5,766,184 A | 6/1998 | Matsuno et al. |
| 5,766,186 A | 6/1998 | Faraz et al. |
| 5,766,209 A | 6/1998 | Devonec |
| 5,776,148 A | 7/1998 | Christy |
| 5,776,150 A | 7/1998 | Nolan et al. |
| 5,776,152 A | 7/1998 | Sekons |
| 5,779,718 A | 7/1998 | Green et al. |
| 5,779,719 A | 7/1998 | Klein et al. |
| 5,782,845 A | 7/1998 | Shewchuk |
| 5,792,400 A | 8/1998 | Talja et al. |
| 5,797,927 A | 8/1998 | Yoon |
| 5,814,054 A | 9/1998 | Kortenbach et al. |
| 5,817,108 A | 10/1998 | Poncet |
| 5,817,110 A | 10/1998 | Kronner |
| 5,817,119 A | 10/1998 | Klieman et al. |
| 5,827,298 A | 10/1998 | Hart et al. |
| 5,830,179 A | 11/1998 | Mikus et al. |
| 5,830,231 A | 11/1998 | Geiges, Jr. |
| 5,836,956 A | 11/1998 | Buelna et al. |
| 5,843,001 A | 12/1998 | Goldenberg |
| 5,843,099 A | 12/1998 | Nichols et al. |
| 5,855,585 A | 1/1999 | Kontos |
| 5,860,992 A | 1/1999 | Daniel et al. |
| 5,868,760 A | 2/1999 | McGuckin, Jr. |
| 5,871,488 A | 2/1999 | Tovey et al. |
| 5,871,490 A | 2/1999 | Schulze et al. |
| 5,879,371 A | 3/1999 | Gardiner et al. |

| | | |
|---|---|---|
| 5,891,160 A | 4/1999 | Williamson, IV et al. |
| 5,899,909 A | 5/1999 | Claren et al. |
| 5,902,311 A | 5/1999 | Andreas et al. |
| 5,904,692 A | 5/1999 | Steckel et al. |
| 5,908,426 A | 6/1999 | Pierce |
| 5,908,428 A | 6/1999 | Scirica et al. |
| 5,911,727 A | 6/1999 | Taylor |
| 5,916,195 A | 6/1999 | Eshel et al. |
| 5,919,199 A | 7/1999 | Mers Kelly et al. |
| 5,931,844 A | 8/1999 | Thompson et al. |
| 5,951,575 A | 9/1999 | Bolduc et al. |
| 5,954,732 A | 9/1999 | Hart et al. |
| 5,964,771 A | 10/1999 | Beyar et al. |
| 5,964,773 A | 10/1999 | Greenstein |
| 5,964,782 A | 10/1999 | Lafontaine et al. |
| 5,980,538 A | 11/1999 | Fuchs et al. |
| 5,980,550 A | 11/1999 | Eder et al. |
| 5,984,917 A | 11/1999 | Fleischman et al. |
| 5,992,419 A | 11/1999 | Sterzer et al. |
| 5,993,464 A * | 11/1999 | Knodel ................. 606/139 |
| 5,993,466 A | 11/1999 | Yoon |
| 6,022,312 A | 2/2000 | Chaussy et al. |
| 6,048,351 A | 4/2000 | Gordon et al. |
| 6,051,006 A | 4/2000 | Shluzas et al. |
| 6,053,900 A | 4/2000 | Brown et al. |
| 6,059,800 A | 5/2000 | Hart et al. |
| 6,071,289 A | 6/2000 | Stefanchik et al. |
| 6,071,305 A | 6/2000 | Brown et al. |
| 6,117,067 A | 9/2000 | Gil-Vernet |
| 6,117,144 A | 9/2000 | Nobles et al. |
| 6,139,536 A | 10/2000 | Mikus et al. |
| 6,224,525 B1 | 5/2001 | Stein |
| 6,245,079 B1 | 6/2001 | Nobles et al. |
| 6,443,962 B1 | 9/2002 | Gaber |
| 6,454,778 B2 | 9/2002 | Kortenbach |
| 6,533,795 B1 | 3/2003 | Tran et al. |
| 6,955,643 B2 | 10/2005 | Gellman et al. |
| 7,410,494 B2 * | 8/2008 | Kalmann et al. ............. 606/205 |
| 2001/0003798 A1 | 6/2001 | McGovern et al. |
| 2001/0020162 A1 | 9/2001 | Mosel et al. |
| 2001/0047147 A1 | 11/2001 | Slepian et al. |
| 2002/0007159 A1 | 1/2002 | Mosel et al. |
| 2002/0007175 A1 | 1/2002 | Chang |
| 2002/0032486 A1 | 3/2002 | Lazarovitz et al. |
| 2002/0032487 A1 | 3/2002 | Dua et al. |
| 2002/0045886 A1 | 4/2002 | Porter |
| 2002/0049425 A1 | 4/2002 | Mosel et al. |
| 2003/0233108 A1 | 12/2003 | Gellman et al. |

FOREIGN PATENT DOCUMENTS

| | | |
|---|---|---|
| EP | 0 482 881 A1 | 4/1992 |
| EP | 0 589 409 | 3/1994 |
| EP | 0 674 875 | 10/1995 |
| EP | 0 935 977 A2 | 8/1999 |
| GB | 2 268 690 | 1/1994 |
| SU | 969254 | 10/1982 |
| SU | 1028320 | 7/1983 |
| SU | 1093329 | 5/1984 |
| SU | 11038 54 A | 7/1984 |
| SU | 1174036 | 8/1985 |
| WO | WO 90/03766 | 4/1990 |
| WO | WO 92/12674 | 8/1992 |
| WO | WO 93/01750 | 2/1993 |
| WO | WO 94/13211 | 6/1994 |
| WO | WO 96/09796 | 4/1996 |
| WO | WO 96/27331 | 9/1996 |
| WO | WO 99/47050 | 9/1999 |
| WO | WO 01/28432 | 4/2001 |

OTHER PUBLICATIONS

Lecture "Human Gross Anatomy and Embryology Pelvic Organs and Pelvic Diaphragm" by Dr. Roberts, University of Minnesota Medical School. Lecture given Fall 2000. Information posted to the Internet before Oct. 17, 2002. Describes pelvic floor area.

GyneFlex™ Instructions: Female Pelvic Floor Muscles. Shows color diagrams of the pelvic floor area. Printed Feb. 7, 2003.

"Physicians/Plastic Surgery/Pelvic Floor Dysfunction," Abington Memorial Hospital. Printed Feb. 6, 2003. Describe shat the pelvic area constitutes.

American V. Mueller publication from The Surgical Armamentarium, Instruments Professional Equipment, p. 3, 1980, American Hospital Supply Corporation.

International Search Report for International Application No. PCT/US03/18486, dated Jan. 27, 2004.

Invitation to Pay Additional Fees for International Application No. PCT/US2005/024998.

International Search Report for International Application No. PCT/US2005/024998, dated Mar. 21, 2006.

Written Opinion of the International Searching Authority for International Application No. PCT/US2005/024998, dated Mar. 21, 2006.

* cited by examiner

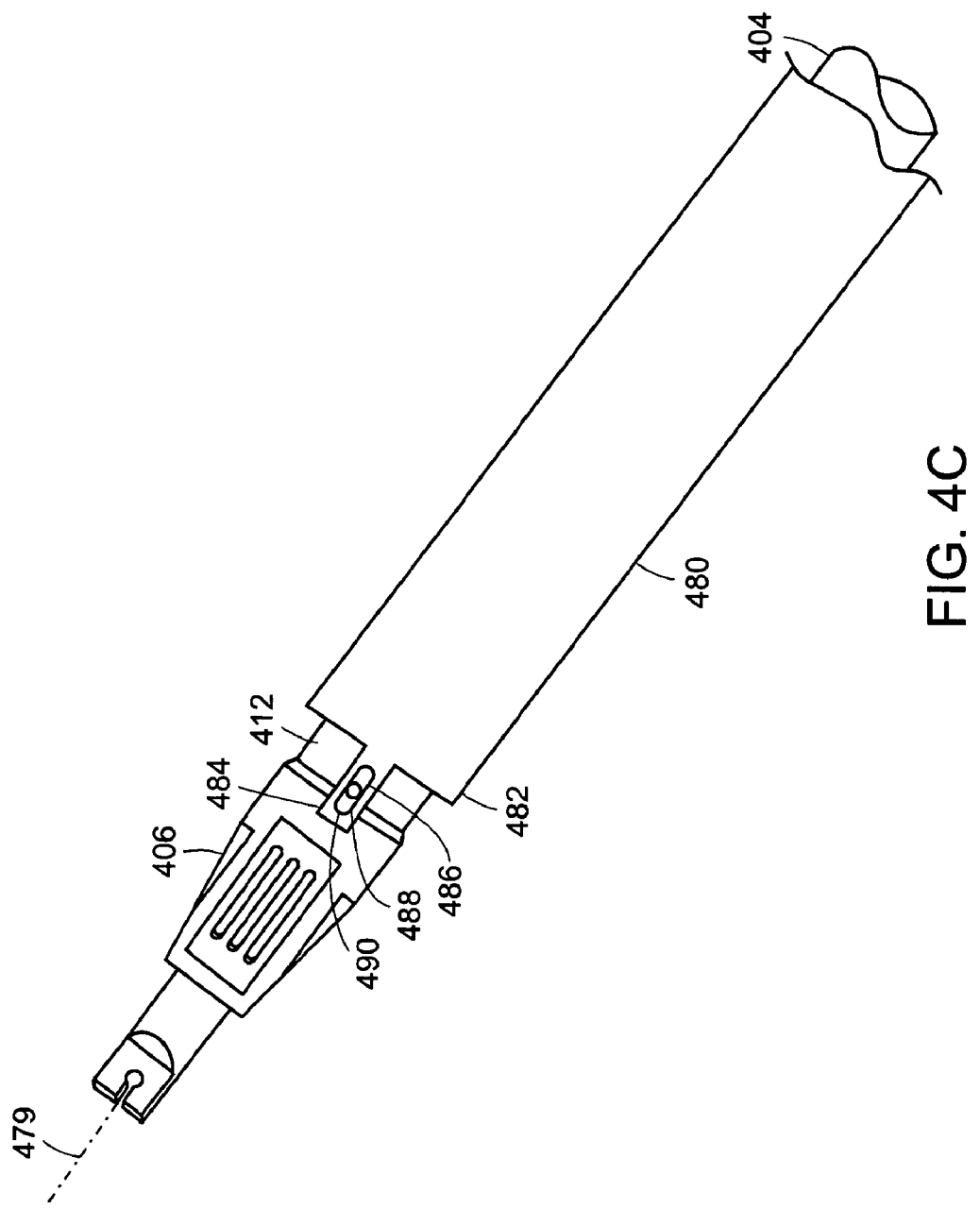

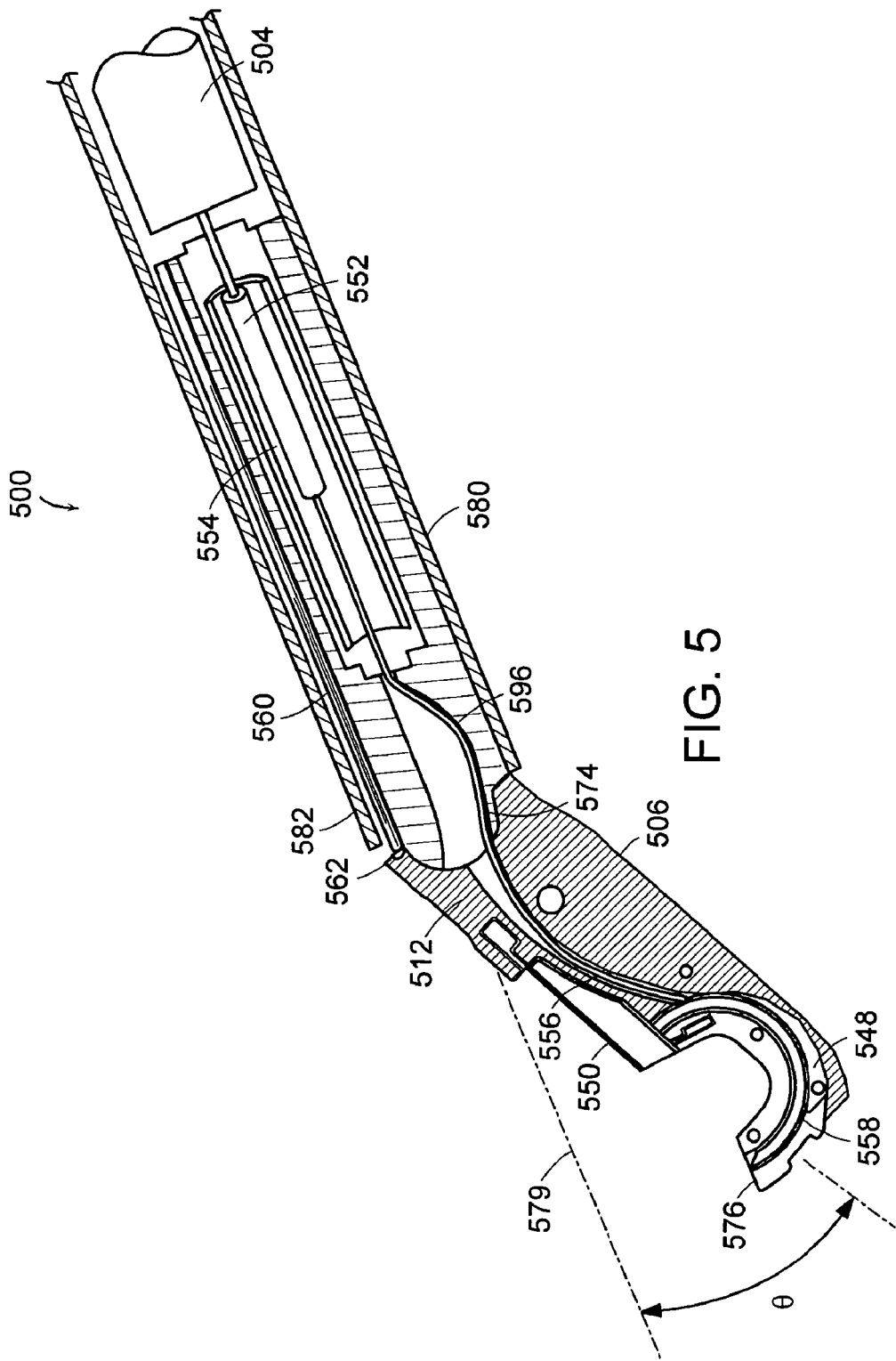

SUTURING INSTRUMENT

This application is a continuation of U.S. application Ser. No. 10/921,517, filed Aug. 19, 2004, now U.S. Pat. No. 8,123,762, the contents of which are incorporated by reference herein in its entirety.

TECHNICAL FIELD

The invention relates to devices and methods for placing sutures.

BACKGROUND INFORMATION

For many surgical procedures, it is necessary to make a large opening in the human body to expose the area that requires surgical repair. There are instruments available that allow for viewing of certain areas of the human body through, for example, a natural body opening or a small puncture wound, and thus avoid the need for making such large openings. These instruments, called endoscopes, can be used in conjunction with specialized surgical instruments to detect, diagnose, and repair areas of the body that previously required open surgery to access.

Some surgical instruments used in endoscopic procedures are limited by the manner in which they access the areas of the human body in need of repair. In particular, the instruments may not be able to access tissue or organs located deep within the body or that are in some way obstructed and inaccessible. In addition, many of the instruments are limited by the way they grasp tissue, apply a suture, or recapture the needle and suture. Furthermore, many of the instruments are complicated and expensive to use due to the numerous parts and/or subassemblies required to enable them to function properly. Suturing remains a delicate and time-consuming aspect of most surgeries, including those performed endoscopically.

Suturing instruments, and more specifically suturing instruments used in endoscopic procedures, are generally rigid and do not provide the operator a range of motion to access difficult to reach parts of the anatomical region requiring sutures. Accordingly, multiple instruments of various configurations and sizes must be used to access all of the necessary tissue areas. These limitations of suturing instruments complicate the endoscopic procedure for the surgeon by requiring the insertion and removal of multiple instruments from a surgical site as the target suturing area changes during the course of the surgical procedure.

SUMMARY OF THE INVENTION

The invention generally relates to a medical device for performing a surgical procedure, such as passing a suture through tissue. More particularly, in one embodiment, the invention is directed to a suturing instrument including an articulating distal portion pivotally coupled to the elongate member for improved maneuverability and functionality during surgery. According to one feature, the suturing instrument is dimensioned and configured to apply sutures to approximate, ligate, or fixate tissue in, for example, open, mini-incision, trans-vaginal, laporoscopic, or endoscopic surgical procedures.

In a first aspect, the invention is directed to a suturing instrument including an elongate member and a sheath slideably disposed about the elongate member. The elongate member includes a longitudinal axis and a distal portion biased offset from the longitudinal axis. The sheath actuates the distal portion of the suturing instrument relative to the longitudinal axis by direct contact with the distal portion.

In one embodiment according to the first aspect of the invention, the distal portion is pivotally coupled to the elongate member. In another embodiment, the distal portion is biased up to about 90 degrees relative to the longitudinal axis. In a further embodiment, the distal portion spans a range of actuation from about 1 degree to about 90 degrees.

In a second aspect, the invention relates to a suturing instrument including an elongate member and a head coupled to a distal portion of the elongate member. A movable sheath is disposed about the elongate member and slideable along a length of the elongate member. The sheath includes a distal end with a tab extending therefrom and a fastener coupling the tab of the sheath to the head. Sliding the sheath in a proximal direction causes the head to pivot.

In various embodiments according to the second aspect of the invention, the fastener couples the tab extending from the sheath via a slot defined by the tab. Sliding the sheath in a proximal direction causes the tab to engage the fastener, thereby pivoting the head. The sheath extends substantially the entire length of the elongate member. In a further embodiment according to this aspect of the invention, sliding the sheath in a proximal direction relative to the elongate member biases the head offset from the longitudinal axis of the elongate member. Sliding the sheath in a distal direction causes the head to pivot into substantial alignment with the longitudinal axis.

In various embodiments according to the foregoing aspects of the invention, the suturing instrument includes a needle deployment mechanism that is at least partially housed in the elongate member. In another embodiment of the invention, the suturing instrument includes a needle carrier and an actuator at least partially disposed within the elongate member and coupled to the needle carrier. The needle carrier may include a distal portion that defines a lumen for receiving the needle. With this arrangement, the needle is advanced out of an opening defined by the head by the actuator. In a further embodiment, the suturing instrument includes a needle catch disposed on the head and configured to receive the needle. The head or distal portion of the suturing instrument may rotate relative to the elongate member. Additionally, the elongate member of the suturing instrument may include a push rod and spring arrangement for biasing the distal portion offset from the longitudinal axis.

In a third aspect, the invention relates to a suturing instrument having an elongate member including a longitudinal axis, a head pivotally coupled to the elongate member, and a needle deployment mechanism at least partially housed within the elongate member. The needle deployment mechanism includes a needle carrier at least partially disposed in the head for holding a needle and a carrier activation wire coupled to the needle carrier and extending along the longitudinal axis of the elongate member. When in tension, the activation wire biases the head offset from the longitudinal axis of the elongate member. When in compression, the activation wire articulates the head relative to the longitudinal axis and preferentially deploys the needle from the head.

In various embodiments according to the foregoing aspect of the invention, the suturing instrument includes a sheath disposed about the elongate member and slideable along a length of the elongate member. The sheath includes a distal end for engaging and articulating the head relative to the longitudinal axis of the elongate member. In additional embodiments, the head of the suturing instrument is biased up to about 90 degrees relative to the longitudinal axis. In another embodiment, the head spans a range of actuation from about one degree to about 90 degrees. In a further embodiment, the suturing instrument includes a needle catch disposed on the head and configured to receive the needle. The needle carrier may include a distal portion that defines a lumen for receiving the needle. In a further embodiment, the head is biased offset from the longitudinal axis by a push rod and spring arrangement at least partially disposed in the elongate member.

Advantages and features of the present invention herein disclosed will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the invention are described with reference to the following drawings, in which:

FIGS. 4B and 4C are detailed schematic views of the distal portion of the suturing instrument of FIG. 4A;

FIG. 5 is a schematic detailed view of a distal portion of another embodiment of a suturing instrument in accordance with the invention.

DESCRIPTION

Embodiments of the invention are described below. It is, however, expressly noted that the invention is not limited to these embodiments, but rather the intention is that variations, modifications, and equivalents that are apparent to a person skilled in the art are also included.

Figure 1:
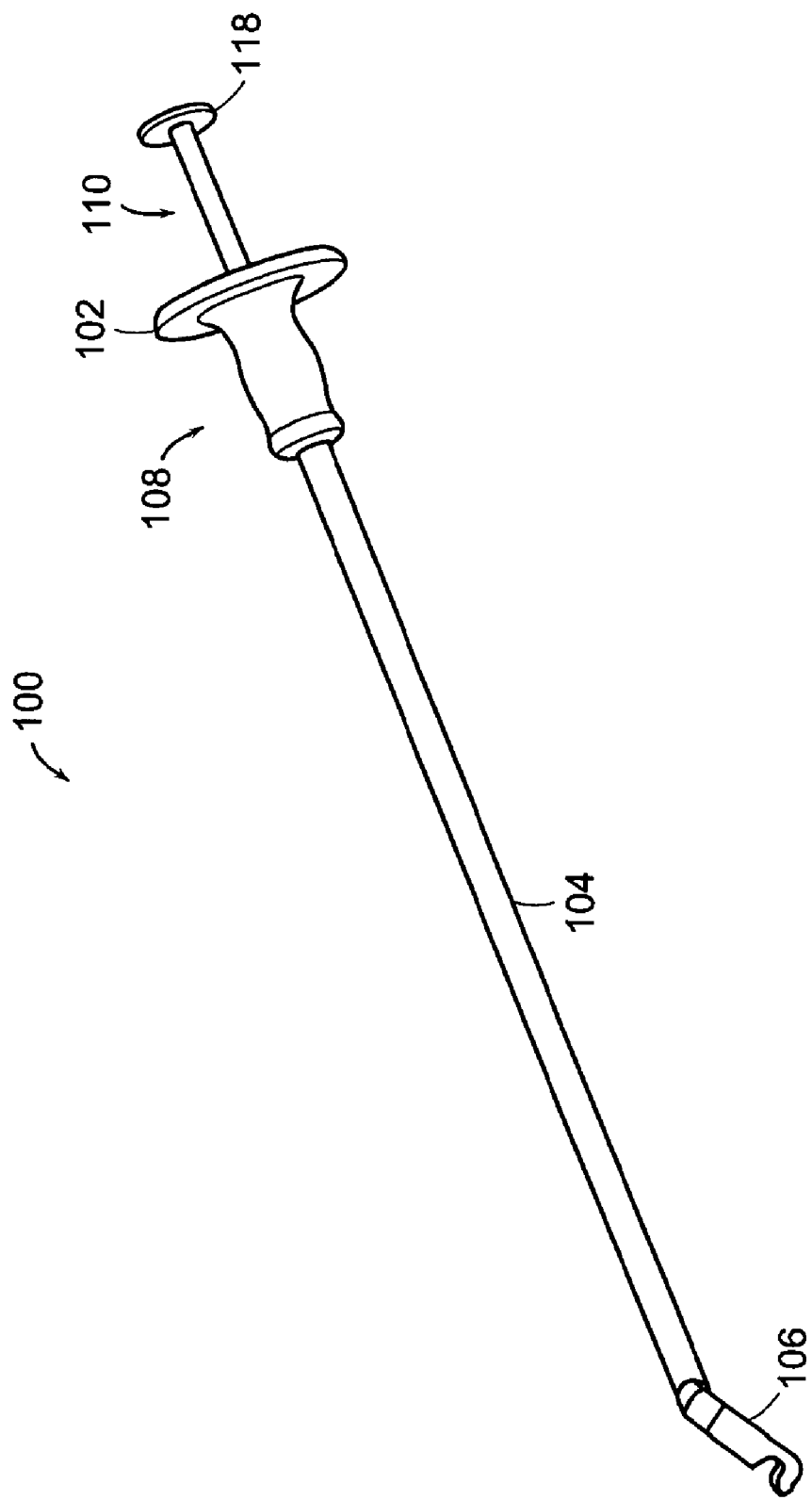
FIG. 1 is a schematic perspective view of one embodiment of a suturing instrument in accordance with the invention.

A suturing instrument according to the invention is used, for example, to access areas within a human body to ligate, fixate, or approximate tissue. The suturing instrument throws one or more stitches intercorporeally. FIG. 1 depicts the general structure of a suturing instrument 100, according to an illustrative embodiment of the invention, including a handle 102, an elongate member 104, a distal portion 106, and a proximal portion 108. The elongate member 104 is mechanically coupled to the handle 102 at the proximal portion 108 and a needle deployment mechanism 110 is at least partially disposed within the distal portion 106 of the suturing instrument 100. The handle 102 may take a variety of forms in various embodiments. For example, the handle 102 may be one of the types used with Boston Scientific Corporation's suturing systems, in particular, those handles used with the Capio® Push & Catch suturing system. The distal portion 106 is pivotally coupled to the elongate member 104. The distal portion 106 is actuated by, for example, an actuation means disposed within the handle 102 or via the needle deployment mechanism 110.

Figure 2A:
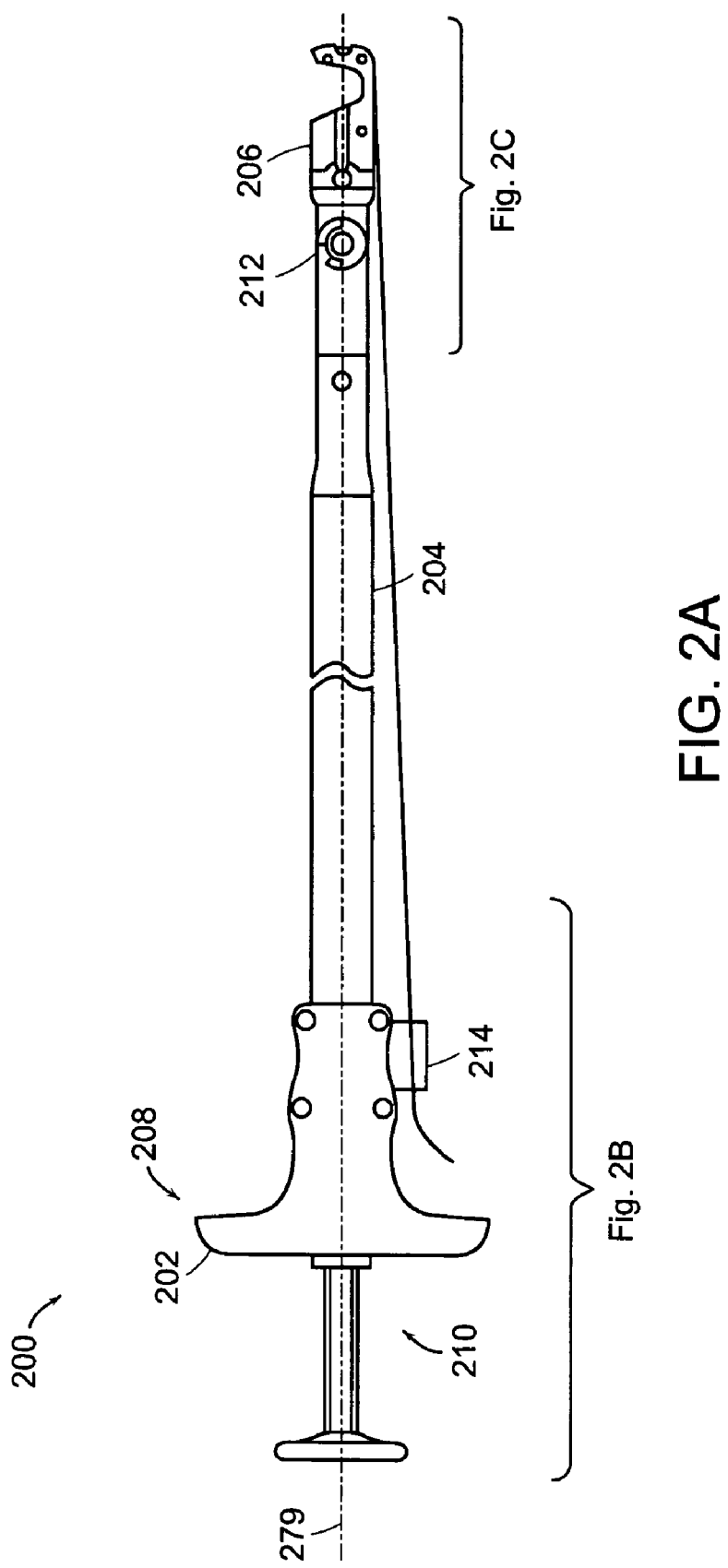
FIG. 2A is a schematic plan view of another embodiment of a suturing instrument in accordance with the invention.

In accordance with one illustrative embodiment of the invention, FIG. 2A depicts a suturing instrument 200 including a handle 202, an elongate member 204, and a needle deployment mechanism 210. The suturing instrument 200 also includes a distal portion 206 and a proximal portion 208. An articulation joint 212 pivotally couples the distal portion 206 to the elongate member 204. The articulation joint 212 may be a clevis, hinge, ball-and-socket joint, or other suitable arrangement, which permits the distal portion 206 to articulate with respect to the elongate member 204. The elongate member 204 is mechanically coupled to the handle 202 at the proximal portion 208 and the suturing components are at least partially disposed within the distal portion 206 of the suturing instrument 200.

Figure 2B:
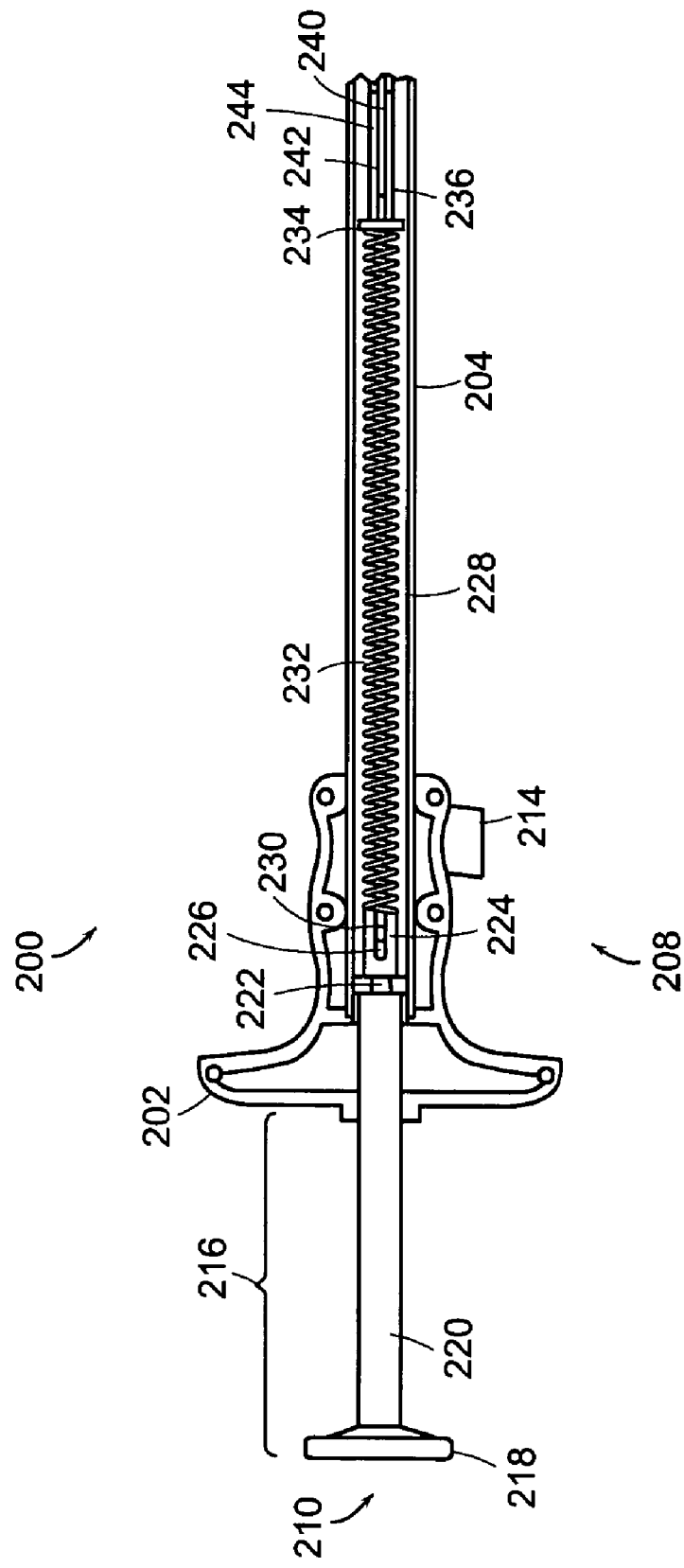
FIGS. 2B and 2C are schematic cross-sectional views of the proximal and distal portions, respectively, of the suturing instrument of FIG. 2A.
Figure 2C:
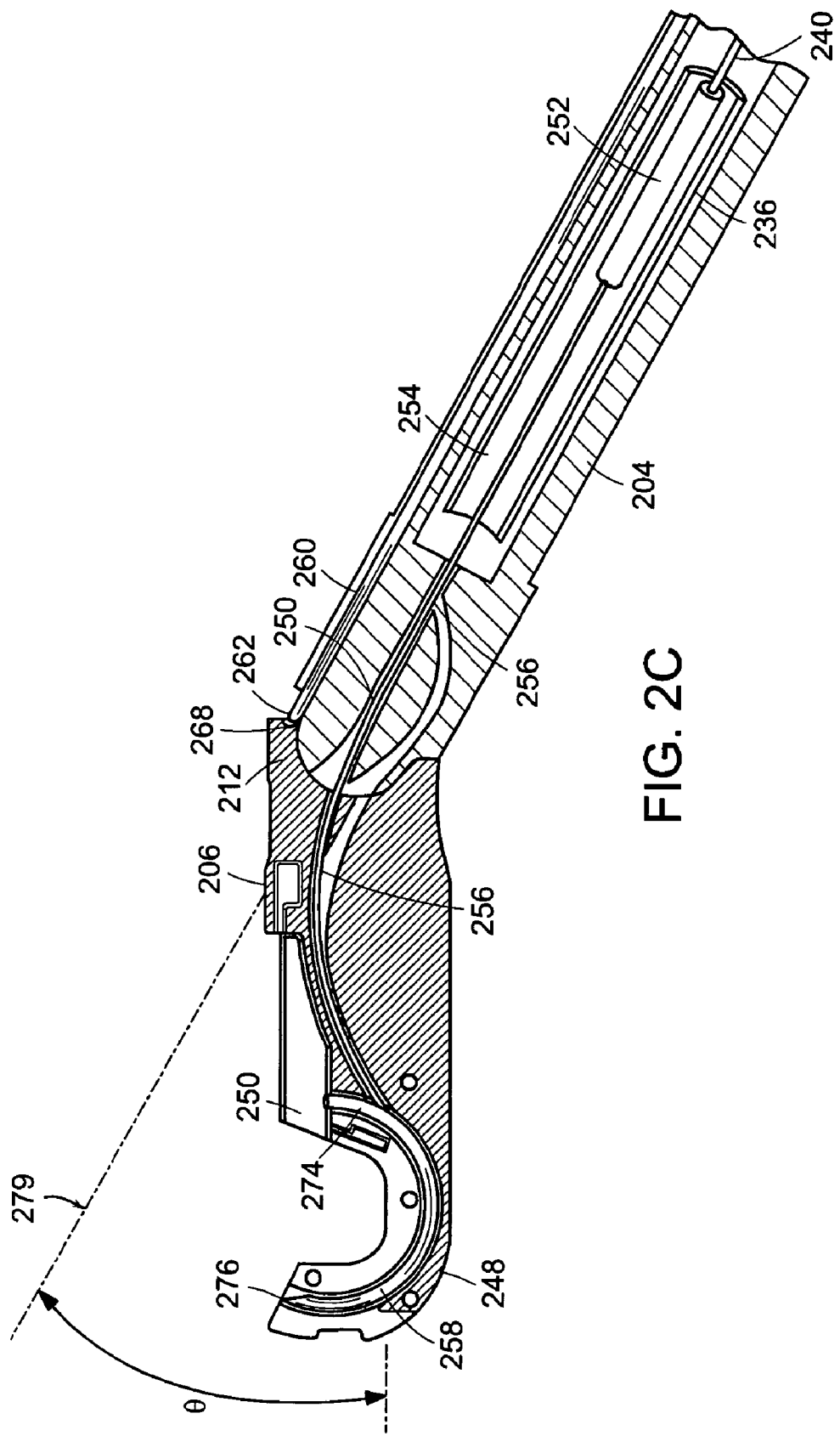

With continued reference to FIG. 2A, the needle deployment mechanism 210 extends longitudinally through the elongate member 204 to the distal portion 206 of the suturing instrument 200, where the needle deployment mechanism 210 is coupled to a needle carrier 258 (see FIG. 2C). The needle deployment mechanism 210 moves the needle carrier 258 between a retracted position and a deployed position.

FIGS. 2B and 2C are cross-sectional views of the proximal portion 208 of the suturing instrument 200 (FIG. 2B) and the distal portion 206 of the suturing instrument 200 (FIG. 2C). Referring first to FIG. 2B, the proximal portion 208 of the suturing instrument 200 includes the handle 202, the elongate member 204, and the needle deployment mechanism 210. In one embodiment, an optional suture clip 214 is coupled to the handle 202 or the elongate member 204 and holds an end of one or more sutures prior to placement in a patient. The needle deployment mechanism 210 includes an actuator 216 (including an actuator button 218 and a shaft 220), a bearing 222, a button end 224, and a hole 226. The bearing 222 rides along a cylindrical surface 228 that is formed by the inside diameter of the elongate member 204. A wireform 230 is inserted into the hole 226 of the shaft 220, coupling it to the actuator button 218. A substantially helical spring 232 encircles the wireform 230, abuts the button end 224, and is compressed between the button end 224 and a push tube 234. The push tube 234 is seated upon a center tube 236 disposed within the elongate member 204. The center tube 236 is housed by the cylindrical surface 228 and is constrained in the distal portion 206. A pusher wire 240 is attached to the wireform 230 by means of a weld, a coupling, adhesive, or other attachment means, and is slidably disposed within a guidance sleeve 242, the sleeve 242 being disposed within a cylindrical surface 244 formed by the inside diameter of the center tube 236. In one embodiment, the pusher wire 240 is constructed of a shape memory material, such as nitinol. Nitinol is a nickel-titanium alloy. Preferably, the shape memory material is chosen for its combination of properties that allow for bendability and high column strength when constrained.

Referring to the illustrative embodiment of the invention depicted in FIG. 2C, the distal portion 206 of the suturing instrument 200 includes the elongate member 204 pivotally connected to the distal portion 206 by the articulation joint 212. The distal portion 206 includes a curved portion 248 and a needle catch 250. The pusher wire 240, disposed within the center tube 236 is attached by welding or other means to a ferrule 252, which is slidably disposed within a track 254. The ferrule 252 is attached to a carrier activation wire 256, which by virtue of its attachment to the ferrule 252 is also slidably disposed within the track 254. The carrier activation wire 256 is mechanically coupled to an extendable needle carrier 258 by a weld, a coupling, adhesive, or other means. The ferrule 252 is slideably disposed about the pusher wire 240. The track 254 provides a bearing surface for the translational movement of the ferrule 252. A push rod 260 is disposed longitudinally along the elongate member 204, having a distal end 262, which engages the distal portion 206 of the suturing instrument 200 at a pocket 268 disposed in the distal portion 206.

The distal portion 206 is pivotally attached to the suturing instrument 200 by the articulation joint 212. The articulation joint 212 is disposed in the elongate member 204 proximate the distal portion 206. The articulation joint 212 facilitates the rotation about an angle θ for positioning of the distal end 206 of the suturing instrument 200 relative to a longitudinal axis 279. In addition, in some embodiments, the elongate member 204 is substantially linear or includes one or more bends to orient specifically the distal portion 206 of the suturing instrument 200 to engage the location of suture placement. The articulation joint 212 and/or bend(s) along the elongate member 204 may facilitate access to deep and/or difficult to reach areas within the human body. The curved portion 248 of the distal portion 206 defines a channel 274 and an opening (or needle exit port) 276. The needle carrier 258 is slideably disposed within the channel 274.

Figure 2D:
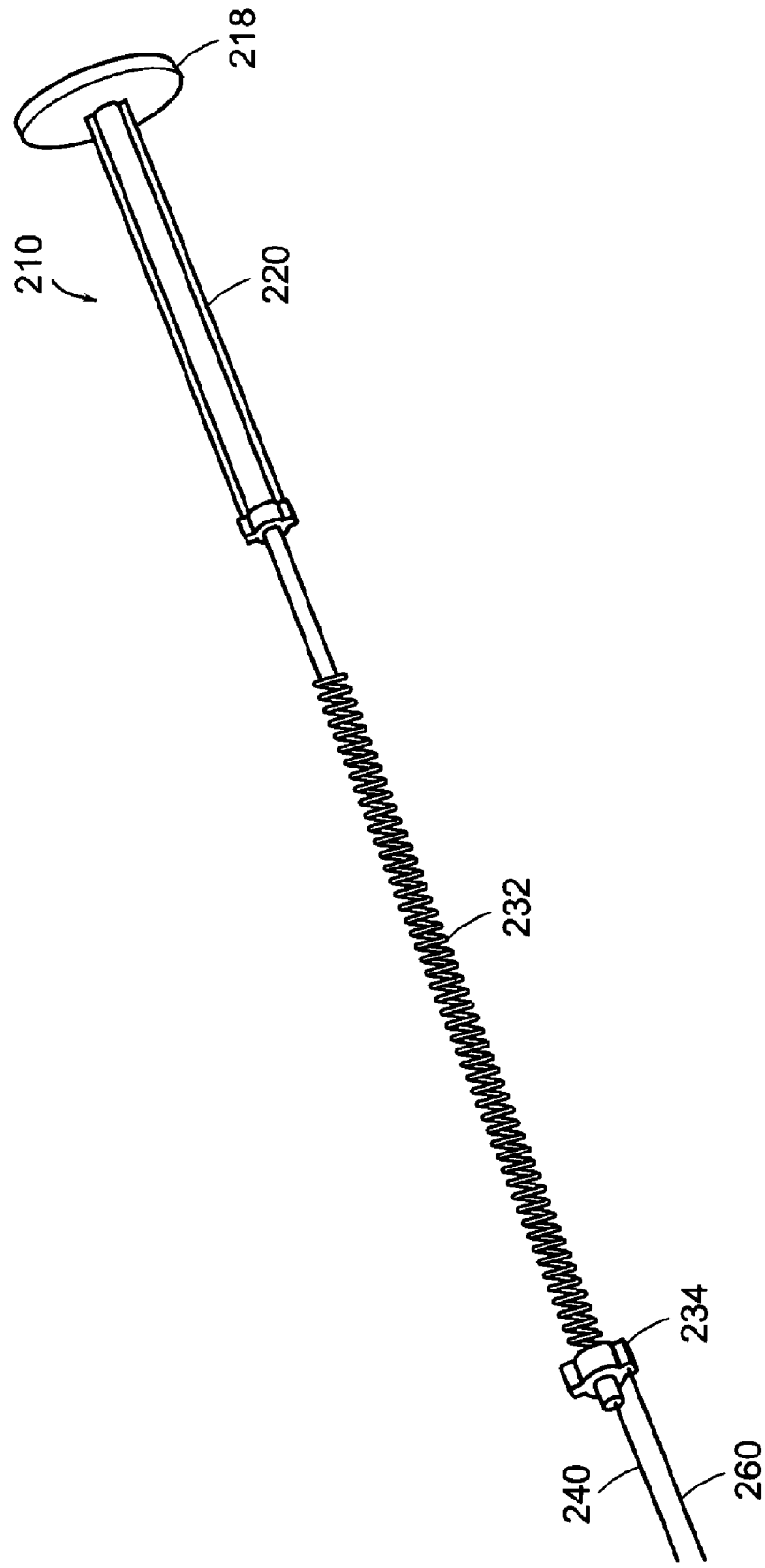
FIG. 2D is a schematic perspective view of various internal components of the suturing instrument of FIG. 2A.
Figure 2E:
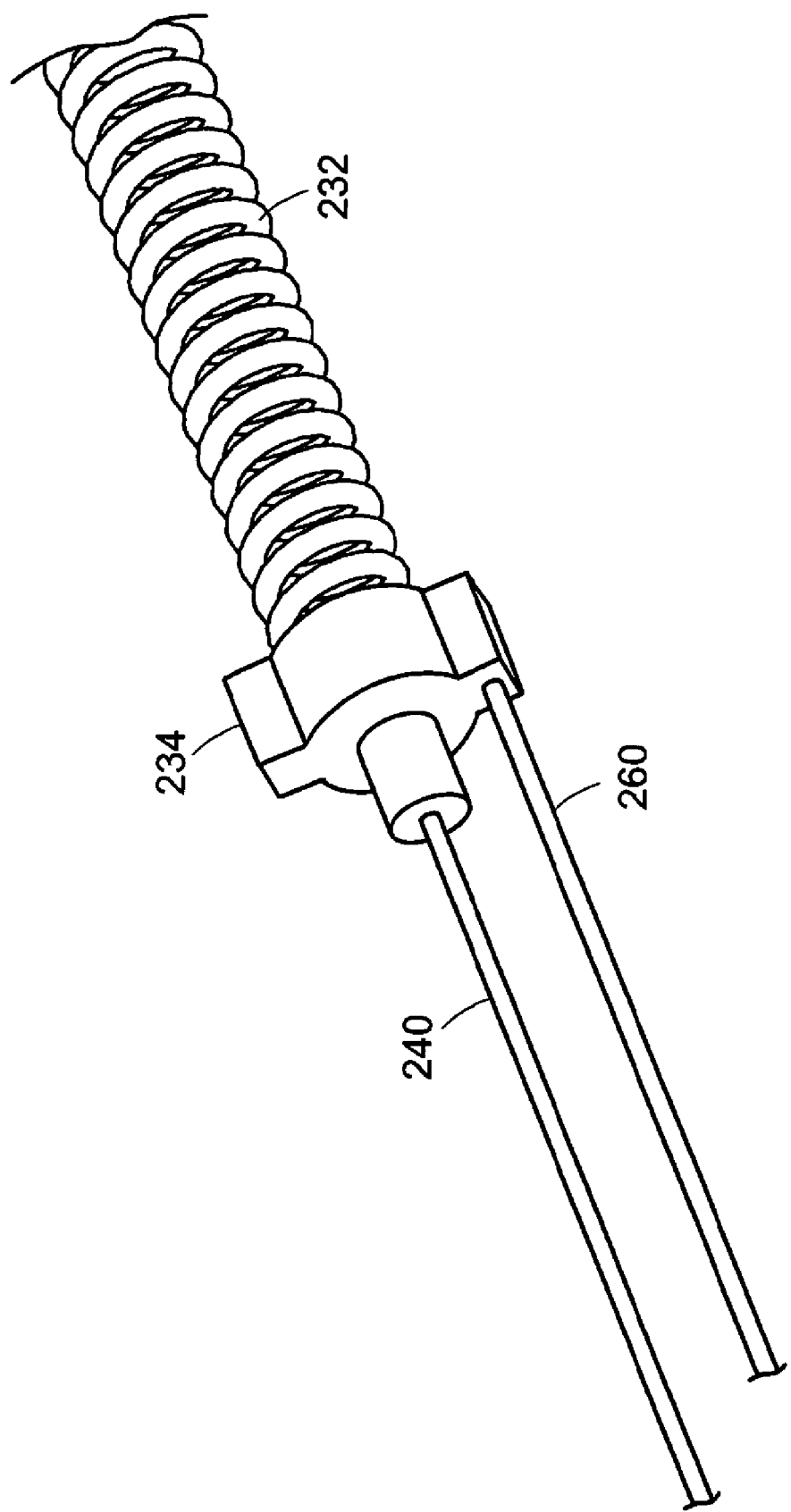
FIG. 2E is an enlarged view of a portion of the suturing instrument of FIG. 2D.

FIGS. 2D and 2E depict the internal assembly of various components of the suturing instrument 200 and the needle deployment mechanism 210 in greater detail. The pusher wire 240 is attached directly to a distal portion of the shaft 220 and the push rod 260 is attached to the shaft 220 at the push tube 234, the push tube 234 being disposed proximate to the distal portion of the shaft 220. There are a variety of ways to secure the pusher wire 240 and push rod 260 to the distal end of the shaft 220, e.g., welding, adhering, and threading. In some embodiments, depression of the button 218 translates to movement along a distal direction of both the pusher wire 240 and the push rod 260.

The operation of the suturing instrument 200 is described with renewed reference to FIG. 2B and continued reference to FIG. 2C. The needle deployment mechanism 210 is actuated by pushing on the button 218, which translates longitudinal movement along the shaft 220 to the pusher wire 240, thereby moving the ferrule 252 along the track 254 and concomitantly moving the carrier activation wire 256 along the channel 274 within the curved portion 248. The carrier activation wire 256 moves the needle carrier 258, through the opening 276. As the pusher wire 240 responds to a larger displacement of the button 218, the ferrule 252 reaches a terminal point as it travels along the track 254 and this action limits the outward travel of the carrier activation wire 254 to prevent overdriving and eliminate the possibility of expelling the needle carrier 258 from the suturing instrument 200. As the button 218 is released, the spring 232 biases the shaft 220 proximally, moving the pusher wire 240, the ferrule 252, and the carrier activation wire 254 proximally along with the shaft 220, and the needle carrier 258 retracts into the channel 274 of the distal portion 206.

With continued reference to FIG. 2C, the distal portion 206 of the suturing instrument 200 may be rotated about the articulation joint 212 by sliding the push rod 260 along a distal direction by pushing on the button 218, which translates longitudinal movement of the shaft 220 to the push rod 260, which is attached to the shaft 220 at the push tube 234 (FIG. 2D). The distal end 262 of the push rod 260 engages the distal portion 206 of the suturing instrument at the pocket 268. The pocket 268 is a recessed area in the distal portion 206 for engagement and retainment of the distal end 262 of the push rod 260 as the distal portion 206 rotates about the articulation joint 212 out of alignment with the longitudinal axis 279 extending through the elongate member 204. In one embodiment, the distal portion 206 is offset at an angle θ of up to about 90 degrees relative to the longitudinal axis 279. In one preferred embodiment, the distal portion 206 is offset at an angle of about 30 degrees relative to the longitudinal axis 279. In one embodiment, the push rod 260 is biased distally by the spring 232 (FIG. 2D) to offset the distal portion 206 out of alignment with the longitudinal axis 279 in a normal state.

Preferably, the suturing instrument's component materials are biocompatable. For example, the handle 202, the elongate member 204, and portions of the needle deployment mechanism 210 may be fabricated from extruded, molded, or machined plastic material(s), such as polypropylene, polycarbonate, or glass-filled polycarbonate. Other components, for example the needle carrier 258, may be made of stainless steel. Other suitable materials will be apparent to those skilled in the art. The type of material(s) used to form a suture is not critical to the present invention, as long as the material is biocompatible. The user selects the length, diameter, and characteristics of the suture to suit a particular application. Additionally, mechanical components and operation such as those disclosed in U.S. Pat. Nos. 5,364,408 and 6,048,351, and commonly owned U.S. patent application Ser. No. 10/210,984, each of which is incorporated by reference herein in its entirety, may be employed with features of the invention.

Figure 3A:
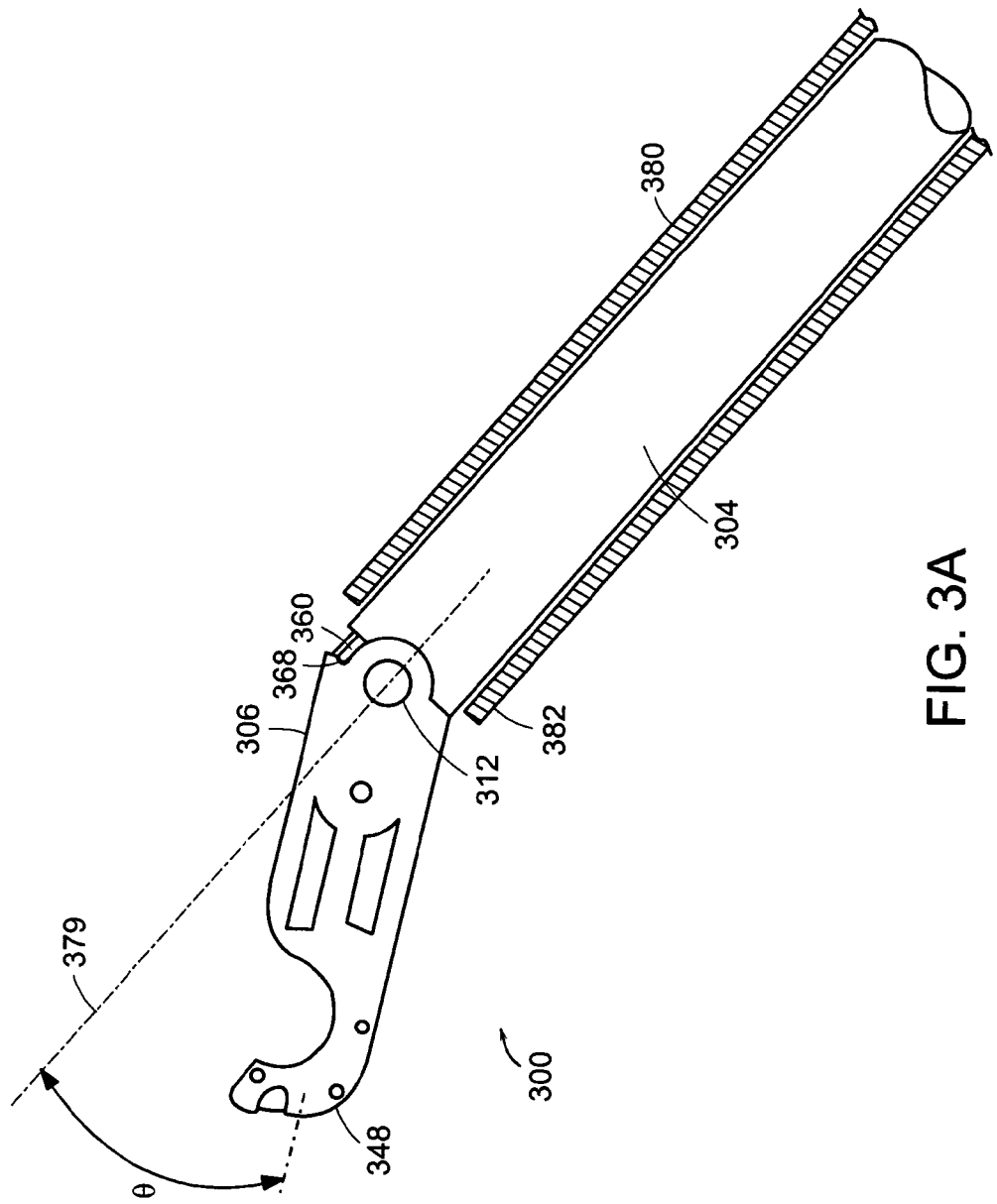
FIGS. 3A to 3C are detailed schematic views of the distal portion of another embodiment of a suturing instrument in accordance with the invention.
Figure 3B:
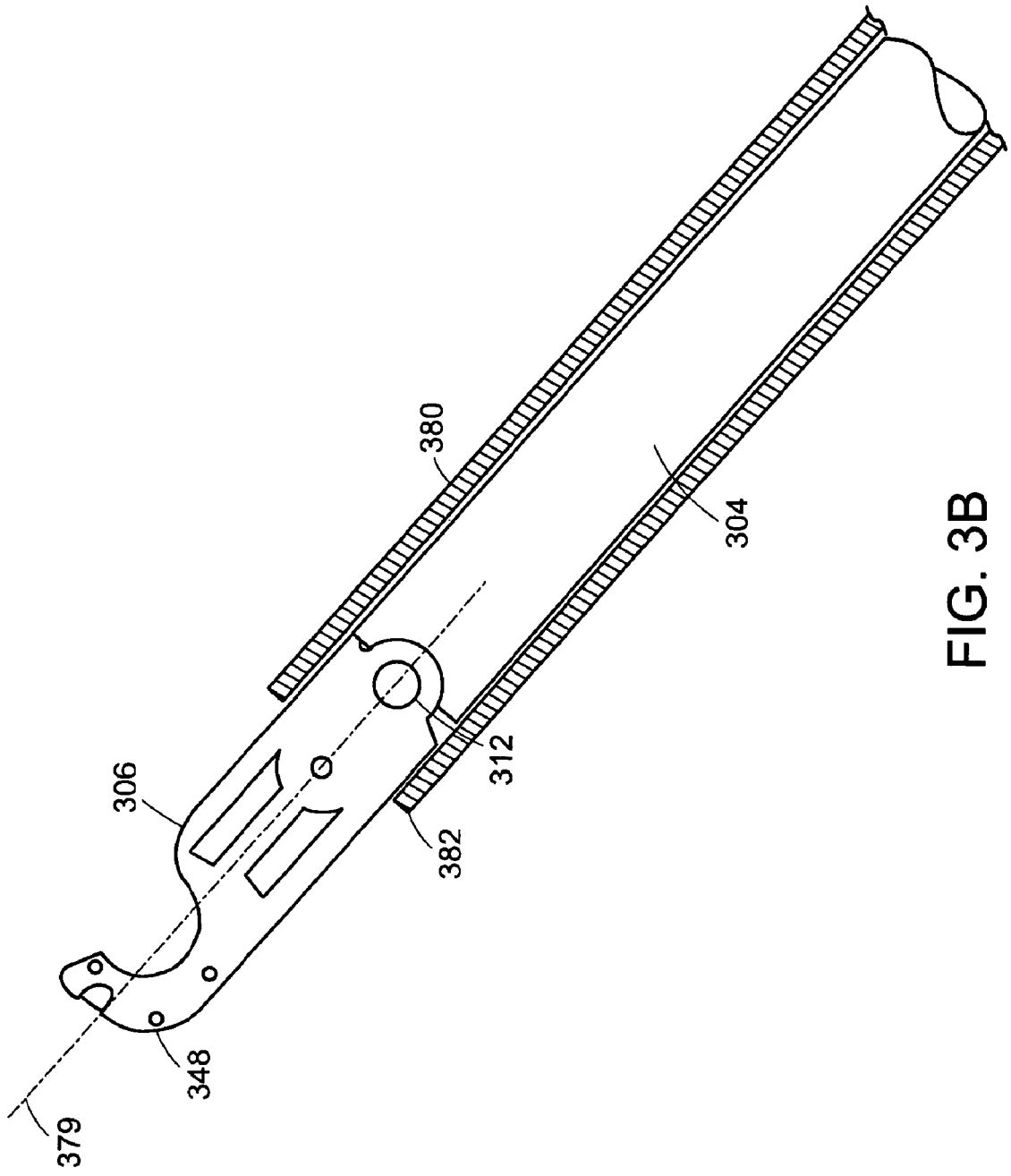
Figure 3C:
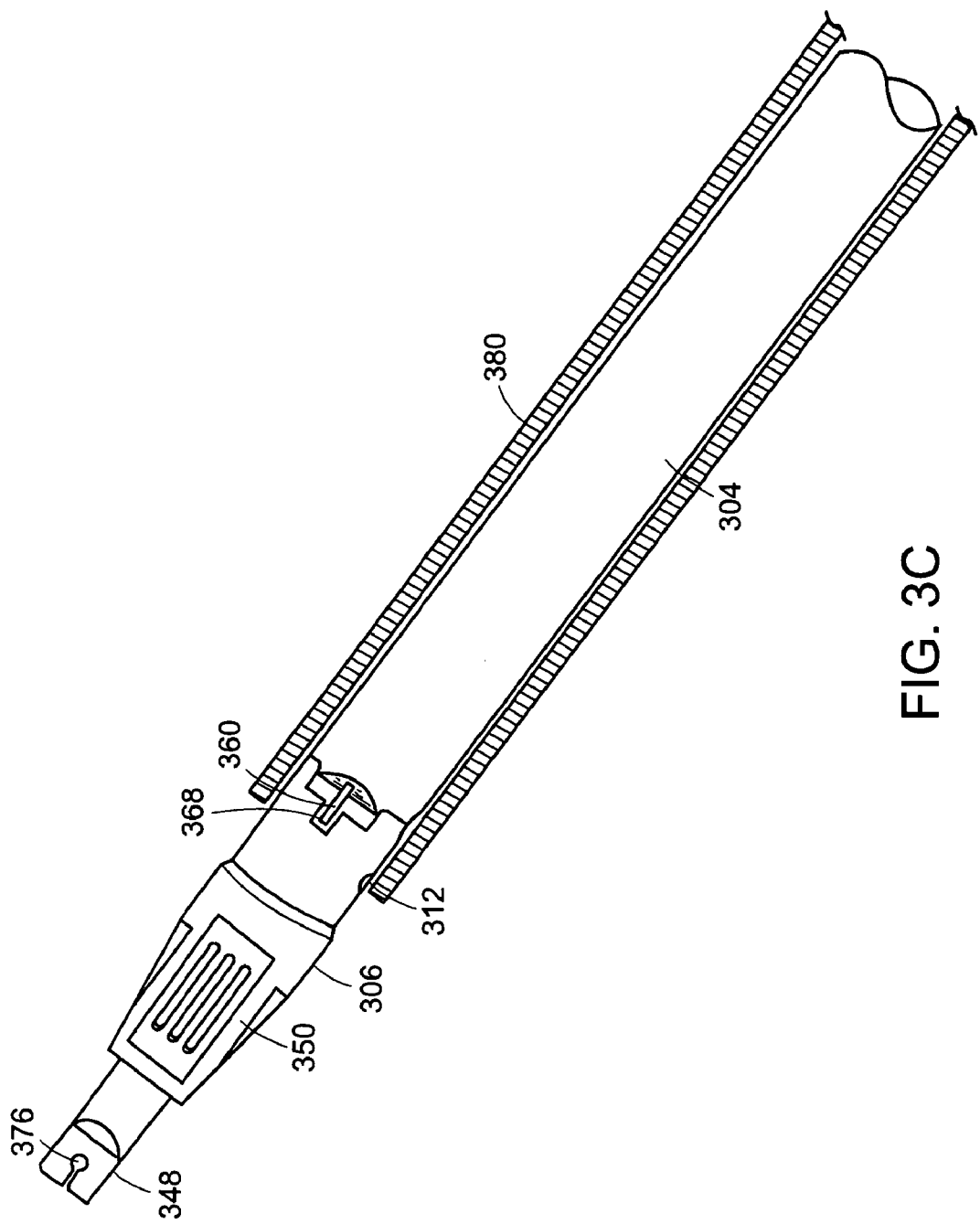

FIGS. 3A to 3C depict another illustrative embodiment of a suturing instrument 300. The elongate member 304 is pivotally connected to the distal portion 306 at the articulation joint 312. The distal portion 306 is offset relative to a longitudinal axis 379 by, for example, the aforementioned push rod arrangement. The suturing instrument 300 includes an external sheath 380 (shown in partial section) disposed about the elongate member 304 and having a distal portion 382 for engaging the distal portion 306 of the suturing instrument 300. The inside diameter of the sheath 380 may be dimensioned such that it slides freely along the elongate member 304 or alternatively, the sheath 380 may be of reduced inside diameter such that a slight friction-fit between the elongate member 304 and the sheath 380 is established. The sheath 380 preferably extends proximally along the elongate member 304 to permit articulation of the distal portion 306 by the user when the suturing instrument 300 is inserted into the body of a patient.

In operation, the sheath 380 is moved by the user in a distal direction along the elongate member 304 until the distal end 382 of the sheath 380 engages the offset distal portion 306 of the suturing instrument 300. As the movement of the sheath 380 continues in a distal direction, the distal portion 306 rotates about the articulation joint 312 into alignment with the longitudinal axis 379 until the distal portion 382 of the sheath 380 is located at a position distal to the articulation joint 312 (FIG. 3B). At this point, the distal portion 306 is substantially colinear to the longitudinal axis 379. The distal portion 306 may be dimensioned such that the distal end 382 of the sheath 380 may not extend past the distal portion 306 thereby avoiding overextension of the sheath 380. For example, the distal portion 306 may include a stop to prevent the sheath 380 from extending past the distal portion 306.

The sheath 380 and the push rod 360 may be operated in conjunction to positively actuate the distal portion 306 of the suturing instrument 300 either out of alignment (using the push rod 360) or into alignment (using the sheath 380) with the longitudinal axis 379 of the elongate member 304. Sliding the push rod 360 in a distal direction along the elongate member 304 engages the pocket 368 of the distal portion 306 of the suturing instrument 300 and effects rotation about the articulation joint 312 out of alignment with the longitudinal axis 379. In alternative embodiments, the push rod 360 is biased in a distal direction or manually actuated such that the push rod 360 is disposed within the elongate member 304 with a friction-fit to provide a predetermined amount of resistance to movement along the longitudinal axis 379 once the desired position of the push rod 360 is set.

Figure 4A:
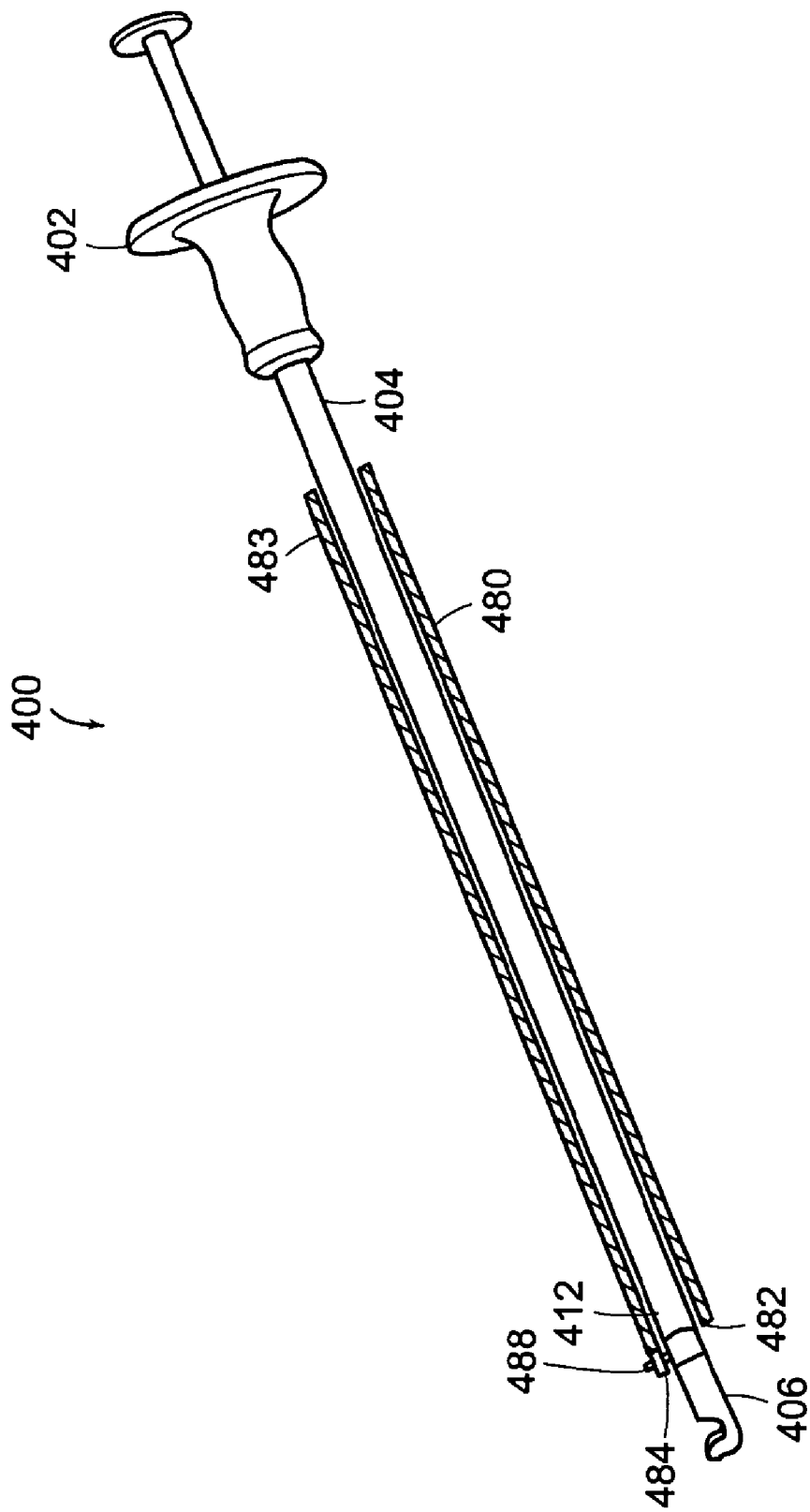
FIG. 4A is a schematic perspective view of yet another embodiment of a suturing instrument in accordance with the invention.
Figure 4B:
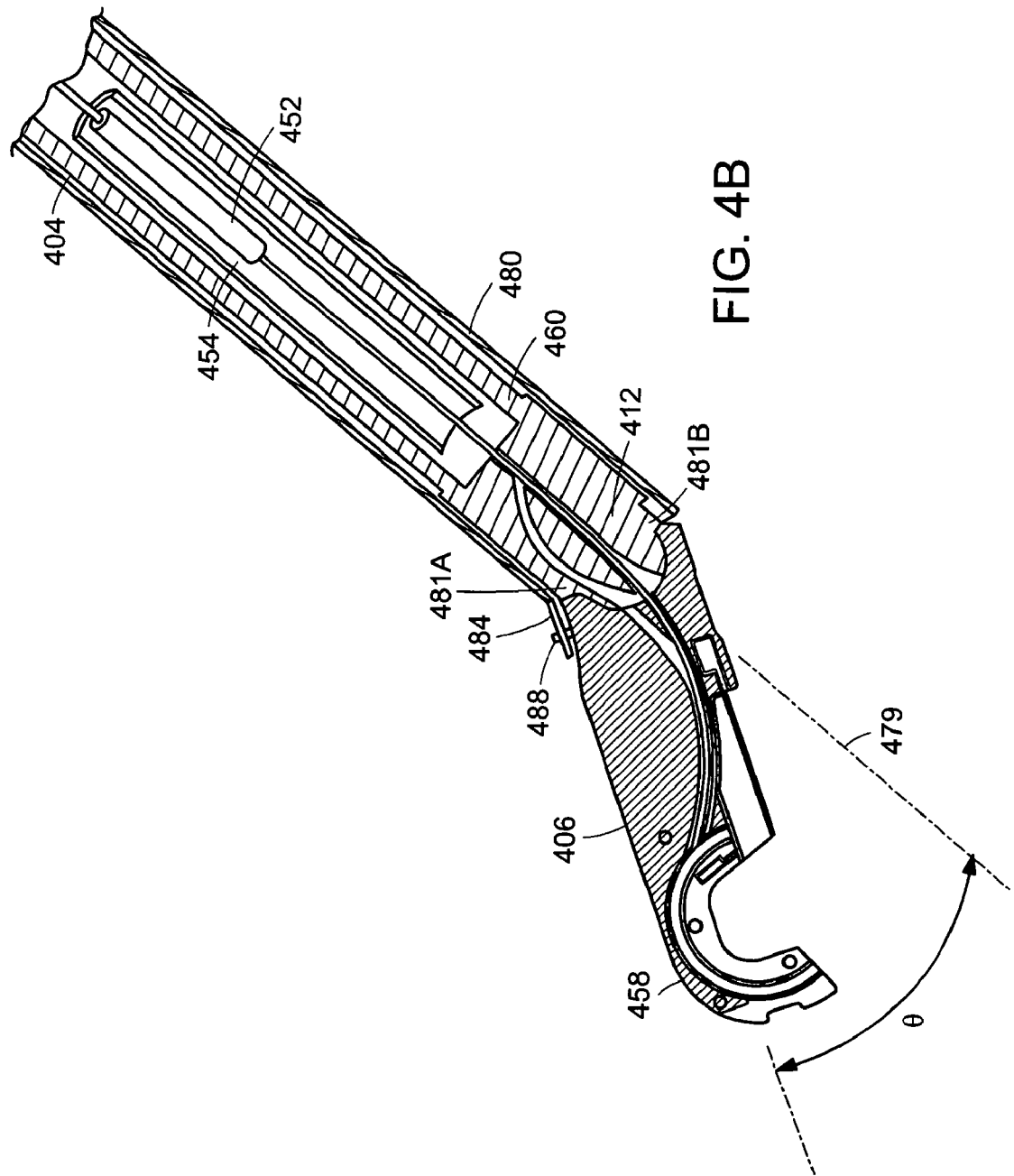

FIGS. 4A to 4C depict another illustrative embodiment of a suturing instrument 400. The suturing instrument 400 includes an external sheath 480 (shown in section) with a distal end 482 and a flexible tab 484 extending distally therefrom. The inside diameter of the sheath 480 may be dimensioned such that it slides freely along the elongate member 404 or alternatively, the sheath 480 may be of a reduced inside diameter such that a slight friction-fit between the elongate member 404 and the sheath 480 is obtained. The sheath 480 is moved along the elongate member 404 by sliding a proximal portion 483 of the sheath 480 toward the distal portion 406. In alternative embodiments, the sheath 480 is moved via an actuation means disposed at least partially in the proximal portion 408. The actuation means for moving the sheath 480 along the elongate member 404 includes, for example, a slideable pin and slot arrangement, a flute or rotational grove disposed on the sheath 480 for engaging a pin on the proximal portion 408 of the elongate member 404, which effects translational movement of the sheath 480 when the sheath 480 is rotated. The suturing instrument 400 also includes a needle catch 450 disposed proximate to the distal portion 206.

The flexible tab 484 includes a slot 486 (FIG. 4C) having a distal end 490 for slideably engaging a fastener 488 that is fixedly attached to the distal portion 406 of the suturing instrument 400. The fastener 488 could be, for example, a pin, screw, rivet, or cleat. In operation, the sheath 480 is moved along the elongate member 404 to effect rotation of the distal portion 406 about the articulation joint 412. As the sheath 480 is moved in a proximal direction toward the handle 402, the tab 484 attached to the sheath 480 slides along the fastener 488, which is disposed within the slot 486 of the tab 484, until the distal end 490 of the slot 486 engages the fastener 488. The length of the slot 486 is dimensioned so at to ensure that a distal end 490 of the slot 486 engages the fastener 488 only after the distal end 482 of the sheath 480 is located proximal to the articulation joint 412. As the distal end 490 of the slot 486 engages the fastener 488, the distal portion 406 rotates about the articulation joint 412 out of alignment with the longitudinal axis 479. The tab 484 is preferably flexible or hinged to help facilitate rotation of the distal portion 406.

A first stop 481A and a second stop 481B (FIG. 4B) prevent overrotation of the distal end 406 beyond a predetermined angular displacement. In one embodiment, the distal portion 406 is offset from an angle θ of about 0 degrees to about 90 degrees relative to the longitudinal axis 479. In one embodiment, the distal portion 406 rotates such that the angle θ is about 30 degrees relative to the longitudinal axis 479. The first and second stops 481A, 481B engage adjacent areas of the distal portion 406 to provide the rotational limit of travel of the distal portion 406, thereby defining the size of the angle θ. The first stop 481A limits the rotation of the distal portion 406 relative to the longitudinal axis 479 in one direction. The second stop 481B limits the rotation of the distal portion 406 relative to the longitudinal axis 479 in an opposite direction. In one embodiment, the first and second stops 481A, 481B are sized and configured to limit the rotation of the distal portion 406 about the articulation joint 412 so that the angle θ is approximately 90 degrees. In another embodiment, the first and second stops 481A, 481B are sized and configured to limit the rotation of the distal portion 406 about the articulation joint 412 so that the angle θ is approximately 30 degrees. Other magnitudes for angle θ are contemplated to suit specific surgical needs.

FIG. 5 depicts another illustrative embodiment of a suturing instrument 500. The suturing instrument 500 includes a carrier activation wire 556 extending longitudinally from the ferrule 552 to the needle carrier 558 in the distal portion 506 of the suturing instrument 500. In this embodiment, a section of the activation wire 556 is routed in an "S" configuration (S-portion) 596 in the distal portion 506 proximate to the articulation joint 512. The S-portion 596 is disposed within the carrier activation wire channel 574. In a preferred embodiment, the activation wire 556 is constructed from nitinol. In addition, the suturing instrument 500 includes a needle catch 550 disposed proximate to the distal portion 506.

In operation, and in one preferred embodiment, the distal portion 506 of the suturing instrument and the needle carrier 558 are both actuated by movement of the carrier activation wire 556 when the button 218 (FIGS. 2D and 2E) is depressed. Prior to depressing the button 218, a tensile force is maintained upon the carrier activation wire 556 by a spring 232 (FIG. 2D). In an alternative embodiment, the carrier activation wire 556 is maintained in tension by a separate compression spring (not shown). In one embodiment, the distal portion 506 is maintained out of alignment with the longitudinal axis 579 so that the angle θ is approximately 30 degrees. The carrier activation wire 556 is not rigidly coupled to the distal portion 506 of the suturing instrument 500, but is retained within the distal portion 506 by the binding force arising from the friction between the carrier activation wire 556 and the channel 574. More particularly, the configuration of the S-portion 596 of the carrier activation wire 556 contained with the channel 574 provides additional binding force to the carrier activation wire 556 resulting from the curvature of the channel 574 in proximity with the S-portion 596. Under tension, the carrier activation wire 556 will occupy the shortest path within the channel 574 thereby biasing the distal portion 506 about the articulation joint 512 and out of alignment with the longitudinal axis 579 at an initial angle θ of about 30 degrees. The tension of the carrier activation wire 556 may retain the distal portion 506 out of alignment with the longitudinal axis 579 at other angles θ.

When the force is initially applied to the actuation button 218, the distal portion 506 begins to rotate about the articulation joint 512 into alignment with the longitudinal axis 579. This rotation continues until the distal portion 506 meets resistance, such as that provided by body tissue (see FIG. 6). Once the resistance to rotation of the distal portion 506 exceeds the binding resistance of the carrier activation wire 556, the distal portion 506 ceases rotation about the articulation joint 512. With the continued application of force, the carrier activation wire 556 moves in a distal direction advancing the needle carrier 558 from the opening 576 and into the body tissue (as shown in phantom in FIG. 6). The threshold resistance required to overcome the binding resistance of the carrier activation wire 556 within the channel 574 may be predetermined and established for particular surgical procedures to effect the performance characteristics of the suturing instrument 500. The selection of materials and surfaces for the channel 574 and the carrier activation wire 556, as well as the curvature of the S-portion 596 may also be varied to change the threshold resistance. In one embodiment, the suturing instrument 500 may include a push rod 560 and a sheath 580 for an alternative or additional means of actuating the distal portion 506 into alignment or out of alignment with the longitudinal axis 579. The structure and operation of the push rod 560 and the sheath 580 are as described in the aforementioned embodiments.

Figure 6:
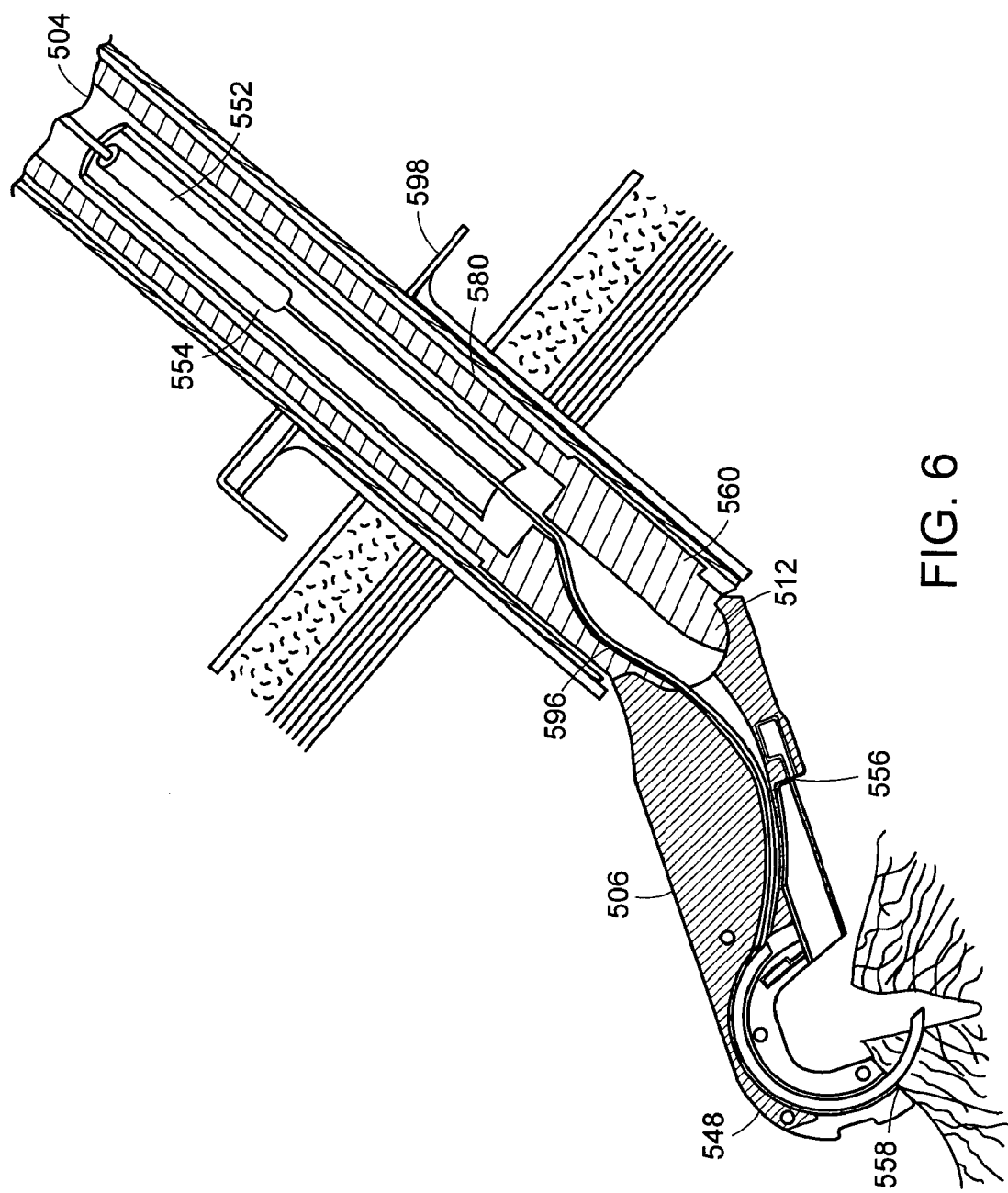
FIG. 6 is a schematic view of a clinical application of the suturing instrument of FIG. 5.

FIG. 6 depicts a clinical application with the suturing instrument 500 of FIG. 5, showing a schematic representation of an endoscopic procedure. The suturing instrument 500 may be inserted into the body through a sleeve 598 (for example, a trocar or cannula) to facilitate access to and from the body cavity. Before the suturing instrument 500 is inserted into the sleeve 598, the distal portion 506 may be articulated such that it is in a substantially linear configuration with respect to the elongate member 504. This may be achieved by using the carrier activation wire 556 as described above or by using the sheath 580 as described in the aforementioned embodiments. Specifically, and in one embodiment, the sheath 580 may be used to straighten the suturing instrument 500 (by rotating the distal portion 506 into alignment with the longitudinal axis 579 without requiring the persistent depression of the actuator button 218 (see FIG. 2B) for maintaining the distal portion 506 in this straightened position. Once the sheath 580 is moved along the elongate member 504 in a distal direction and the suturing instrument 500 is substantially linear, the instrument 500 may be inserted into the sleeve 598. Once inserted, the sheath 580 is moved along the elongate member 504 in a proximal direction until the distal portion 506 is out of alignment with the longitudinal axis 579. The distal portion 506 is now ready for articulation within the body cavity. After inserting the suturing instrument 500 through the opening of the sleeve 598 and into the body, the distal end 506 may be rotated about the articulation joint 512 by any of the aforementioned means, individually or in combination. The suturing instrument 500 may be operated in either the offset or linear configuration. For example, the needle carrier 558 may be advanced when the distal portion 506 is either out of alignment with or in alignment with the longitudinal axis 579. In further embodiments, the needle carrier 558 may be advanced when the suturing instrument 500 is in an intermediate position between the offset and linear configurations.

Other embodiments incorporating the concepts disclosed herein may be used without departing from the spirit and scope of the invention. The described embodiments are to be considered in all respects as only illustrative and not restrictive. Therefore, it is intended that the scope of the invention be only limited by the following claims.

What is claimed is:

1. A suturing instrument comprising:
   an elongate member including a proximal end, a distal end and a longitudinal axis extending therebetween;
   a distal portion pivotably coupled to the distal end of the elongate member via an articulation joint and defining a needle exit port, the distal portion biased in a configuration extending along the longitudinal axis; and
   an actuation mechanism for offsetting the distal portion from the longitudinal axis, the actuation mechanism comprising an external sheath slideably disposed about the elongate member, the sheath positioned in contact with the distal portion to offset the distal portion from the longitudinal axis, whereby when the sheath is slid in a distal direction relative to the elongate member the distal portion is offset from the longitudinal axis, and whereby sliding the sheath in a proximal direction allows the distal portion to return to its biased position along the longitudinal axis.

2. The suturing instrument of claim 1, wherein the articulation join comprises a clevis, a hinge, or a ball-and-socket joint.

3. Thus suturing instrument of claim 1, wherein the external sheath comprises a tab extending distally from the external sheath, the tab comprising a slot configured for engaging a fastener fixedly attached to the distal portion.

4. The suturing instrument of claim 3, wherein the tab is flexible or hinged.

5. The suturing instrument of claim 3, wherein the fastener is a pin, a screw, a rivet or a cleat.

6. The suturing instrument of claim 1, wherein the distal portion comprises a range of actuation from about 1 to about 90 degrees relative to the longitudinal axis.

7. The suturing instrument of claim 1, further comprising at least one stop mechanism disposed at least partially within the elongate member for limiting the range of actuation of the distal portion relative to the longitudinal axis.

8. The suturing instrument of claim 7, wherein the at least one stop mechanism limits the range of actuation of the distal portion from about 1 to about 30 degrees relative to the longitudinal axis.

9. The suturing instrument of claim 7, comprising a first stop mechanism and a second stop mechanism disposed at least partially within the elongate member, the first stop configured for limiting the range of actuation of the distal portion relative to the longitudinal axis in one direction, the second stop configured for limiting the range of actuation of the distal portion relative to the longitudinal axis in an opposite direction relative to the first stop.

* * * * *